United States Patent
Schoo et al.

(10) Patent No.: US 7,723,711 B2
(45) Date of Patent: May 25, 2010

(54) DISPOSABLE OPTICAL SENSOR AND METHOD OF MANUFACTURING SAME

(75) Inventors: Harmannus Franciscus maria Schoo, Eersel (NL); Jacobus Johannes Frederik Van Veen, Badhoevedorp (NL); Hermanus Hendricus Petrus Theodorus Bekman, Purmerend (NL)

(73) Assignee: Nederlandse Organisatie voor toegepast-natuurwetenschappelijk Onderzock TNO, Delft (NL)

( * ) Notice: Subject to any disclaimer, the term of this patent is extended or adjusted under 35 U.S.C. 154(b) by 314 days.

(21) Appl. No.: 10/561,079

(22) PCT Filed: Jun. 17, 2004

(86) PCT No.: PCT/NL2004/000431
§ 371 (c)(1),
(2), (4) Date: Feb. 9, 2006

(87) PCT Pub. No.: WO2005/015173
PCT Pub. Date: Feb. 17, 2005

(65) Prior Publication Data
US 2007/0102654 A1    May 10, 2007

(30) Foreign Application Priority Data
Jun. 17, 2003   (NL) .................................. 1023680

(51) Int. Cl.
*G01N 15/06*   (2006.01)
*G01N 1/00*    (2006.01)

(52) U.S. Cl. ..................................... 250/576; 73/64.56

(58) Field of Classification Search .............. 250/216, 250/225, 573, 574, 575, 576; 356/402, 416, 356/445, 446; 422/82.05, 82.06, 82.07, 82.08, 422/82.9, 82.11; 73/64.56
See application file for complete search history.

(56) References Cited

U.S. PATENT DOCUMENTS

| | | | |
|---|---|---|---|
| 5,039,490 A | | 8/1991 | Marsoner et al. |
| 6,045,756 A | * | 4/2000 | Carr et al. ................. 422/82.11 |
| 6,082,185 A | * | 7/2000 | Saaski ........................ 73/64.56 |
| 6,331,438 B1 | | 12/2001 | Aylott et al. |
| 6,485,687 B1 | * | 11/2002 | Spangenberg et al. .... 422/82.05 |

FOREIGN PATENT DOCUMENTS

WO    WO 02/42747 A1  *  5/2002

OTHER PUBLICATIONS

Saren Johnston, Sensible Sensors, Ames Laboratory Insider Newsletter vol. 13, No. 3 (Mar. 2002), available at http://www.ameslab.gov/final/News/Insider/insider3-02sensiblesensors.htm.*
Savvate'ev et al. (Dec. 2002) Applied Physics Letters 81(24):4652-4654.
Yu et al. (Mar. 1994) Applied Physics Letters 64(12):1540-1542.

* cited by examiner

*Primary Examiner*—Thanh X Luu
(74) *Attorney, Agent, or Firm*—Swanson & Bratschun, L.L.C.

(57) ABSTRACT

The invention relates to an optical sensor comprising at least one detection module which comprises an organic light emitting diode (1) and an organic detection photodiode (2, 2*a*) for measuring emitted light which during the use of the sensor reaches the photodiode via the sample holder. Optionally, a sensor according to the invention further comprises a plastic waveguide.

21 Claims, 5 Drawing Sheets

DISPOSABLE OPTICAL SENSOR AND METHOD OF MANUFACTURING SAME

RELATED APPLICATIONS

Figure 1B:
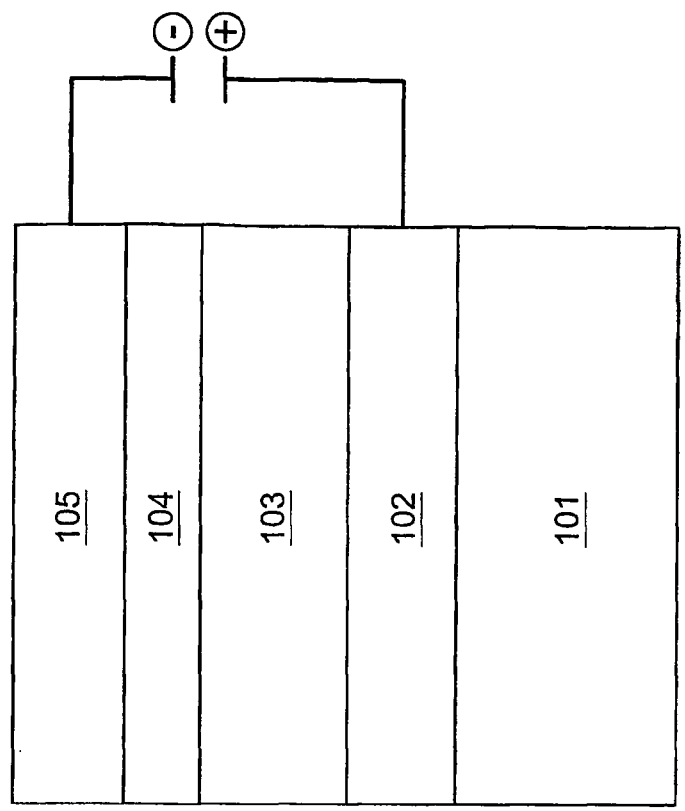

This application is a 35 U.S.C. §371 national phase application of International PCT Application Serial Number PCT/NL2004/000431 (WO 2005/015173), filed on Jun. 17, 2004, entitled "Sensor Comprising Polymeric Components", which application claims priority to Netherlands patent application serial number 1023680, filed Jun. 17, 2003, both of which are incorporated herein by reference in their entirety.

The invention relates to a sensor having polymeric components.

Classic optical sensors are generally assembled from components which have been previously manufactured separately, such as a light source (for instance an incandescent lamp, a LED or a LASER), a photosensitive measuring cell (for instance a photomultiplier tube or a photodiode), a holder for a component to be measured (for instance a cuvette) and other optical components such as a prism or a (light) waveguide. The assembly costs and the fact that the components are usually manufactured with a view to use in relatively expensive systems render such sensors unattractive for use in systems where the price of the system plays a large role, such as, for instance, in disposable sensors.

U.S. Pat. No. 6,331,438 describes an optical sensor having as light source a thin layer of an electroluminescent material such as an organic material. The emitted light is detected by macroscopic detectors such as CCD cameras and photomultiplier tubes (PMT). Such detectors have as a disadvantage, besides their size, that they are expensive and moreover are poorly operable when a voltage is applied across the measuring cell.

It is an object of the invention to provide a new sensor which can serve as an economically attractive alternative to an existing sensor.

It has been found that this object is achieved by providing an optical sensor having a particular type of light emitting diode and a particular type of detection photodiode.

Accordingly, the present invention relates to an optical sensor having at least one detection module which comprises an organic, preferably polymeric, light emitting diode (1) and an organic, preferably polymeric, detection photodiode (2, 2a) for measuring emitted light which during the use of the sensor reaches the photodiode via the sample holder.

It has been found that such a system is very suitable as sensor system for measuring a particular component or measuring a particular physical parameter, such as, for instance, the temperature.

Furthermore, it has been found that such a system can be built up integrally, by one or more relatively simple process steps.

Integral build-up is herein understood to mean that a part can be provided directly on another part of the sensor, without such a part first being manufactured separately and then being used for the assembly of a sensor. Thus, for instance, an OLED and/or a photodiode can be manufactured directly on a waveguide or on a carrier material for the sensor. This makes it possible to manufacture a sensor having an attractive cost price.

An advantage of integral build-up is the relatively simple miniaturization, in particular compared with a sensor based on an inorganic photodiode and LED.

A sensor according to the invention is furthermore very suitable for measuring a component or physical parameter in a liquid, preferably an aqueous medium, or in a gas, preferably air.

It has been found that a sensor according to the invention exhibits a good stability under the influence of variations in ambient factors.

Stability is the extent to which a detection system is resistant to changes in the detection system, influences from the sample and influences from the environment. According as a system is more stable, the noise will be less and/or fewer artifacts will occur in the measuring signal, such as spikes, base line drift and/or base line shifts.

Sensitivity of a detection system is the extent to which the measured signal changes upon a particular change in the concentration or amount of the substance to be detected.

The detection limit is the lowest measurable concentration or amount of a substance. It is determined by the signal to noise ratio. In general, the detection limit for a particular substance is set at a signal to noise ratio of 2 (if the noise is represented as peak to peak) or 4 (if the noise is represented as the root of the mean square noise (RMS noise)).

The term polymer is herein understood to mean a molecule, in particular an organic molecule, which is built up from at least two monomeric units, preferably at least 10 monomeric units. The upper limit is not particularly critical and can be, for instance 1,000,000 or more monomeric units.

FIG. 1 schematically shows a possible build-up for an OLED or a photodiode, with FIG. 1B showing a preferred embodiment.

Figure 2:
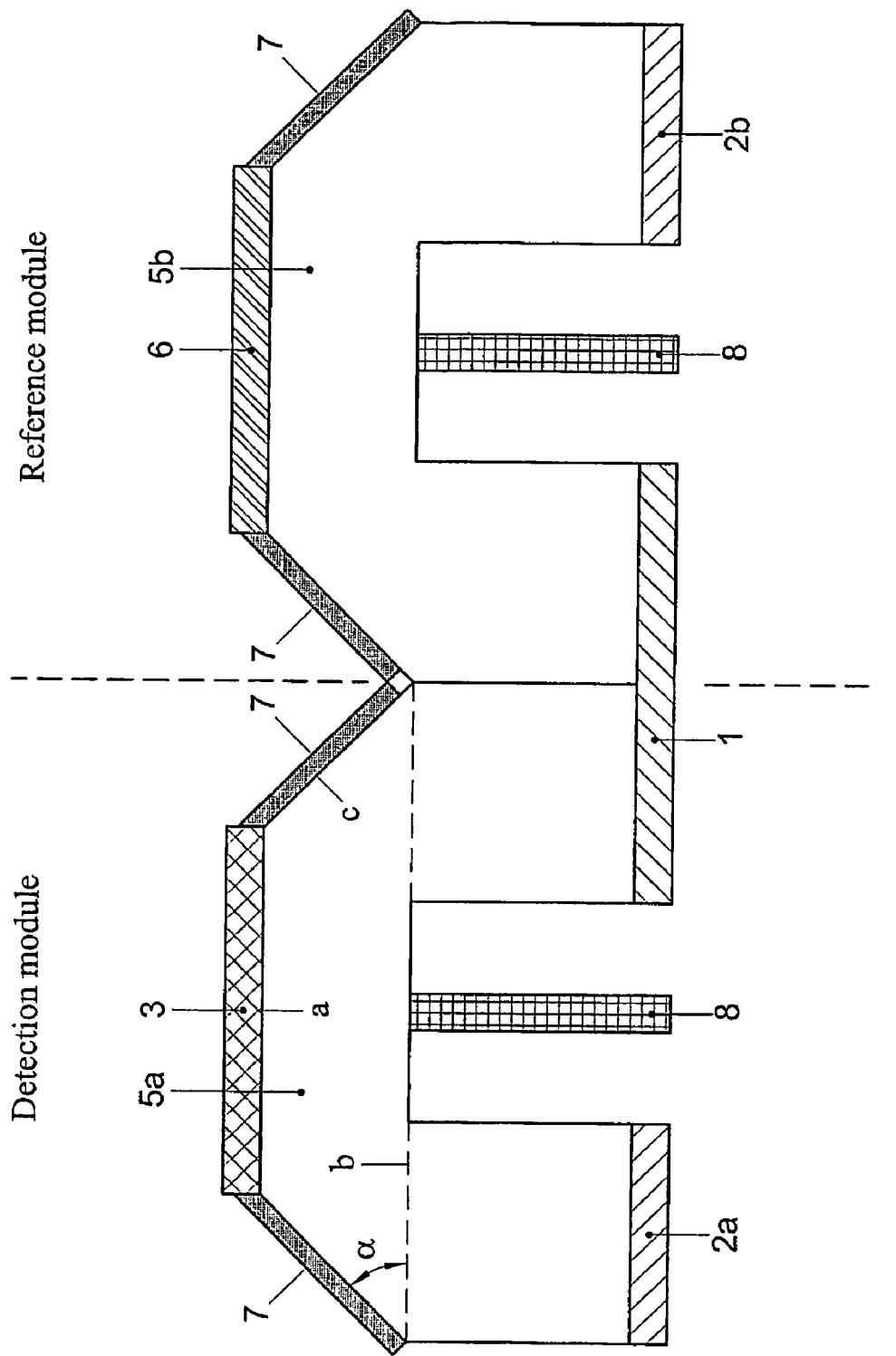

FIG. 2 schematically shows an example of an optical portion (detection module plus reference module) for a sensor according to the invention.

FIGS. 3A-3G schematically show a number of preferred embodiments of (optical portions of) sensors according to the invention.

An organic light emitting diode (hereinafter OLED) is herein understood to mean a light emitting diode whose photoactive layer consists at least substantially of at least one (semi)conductive electroluminescent organic compound or composition. A polymeric light emitting diode (hereinafter called PLED) is herein understood to mean a light emitting diode whose photoactive layer consists at least substantially of at least one (semi)conductive electroluminescent organic polymer (including polymer mixtures) or at least one (semi) conductive organic polymer (including polymer mixtures) and at least one other organic compound (for instance a single compound), which is electroluminescent.

Preferred electroluminescent compounds are polyarylenes, more preferably poly(paraphenylene vinylene) compounds (PPV compounds), polyacetylenes, polyanilines, polythiophenes, polyfluorenes, polyvinylcarbazoles, copolymers thereof and mixtures thereof.

In a preferred embodiment, the OLED has at least two maxima. Light of a wavelength on or near one maximum can then serve, for instance, as a reference signal, and light of a wavelength at another maximum can then serve as detection signal. An OLED with more than one maximum can be provided for in that the OLED contains at least one electroluminescent active layer which comprises at least two different electroluminescent functionalities. Thus, for instance, the photoactive layer can contain a mixture of two different electroluminescent compounds. Examples include mixtures of the polymers mentioned herein, mixtures of the polymers mentioned herein with other electroluminescent compounds, for instance single conjugated compounds, and copolymers with different electroluminescent segments.

An organic and polymeric photodiode, respectively (hereinafter called photodiode) is herein understood to mean a photodiode whose active layer consists at least substantially of at least one (semi)conductive organic compound (including a composition thereof), and of at least one (semi)conductive organic polymer (including a composition thereof), respectively.

The photodiode can comprise as active layer a material (such as a conductive polymer) which exhibits photoconduction when it is under an electric potential.

More preferably, the photodiode is a photovoltaic cell, which, without an electric potential present, exhibits photoconduction and is capable of converting photon energy into electric energy. In such a cell, as electron-donating material and preferably also as electron-accepting material, an organic compound, more preferably an organic polymer, is present. Electron-donating and electron-accepting material can be mixed or be present in separate layers.

Preferably, a photodiode is selected from the group consisting of photodiodes having in the photoactive layer a polymer selected from the group consisting of polyarylene compounds, poly(paraphenylene vinylene) compounds, polyfluorene compounds, polyacetylene compounds, polythiophene compounds, polypyrroles, polyanilines, including derivatives of said polymers (in particular alkyl, aryl and alkoxy derivatives), copolymers of said polymers and said polymers which have been derivatized with a dye In a photovoltaic cell, such polymers have been found very suitable as electron-donating compound.

Good results have been obtained inter alia with a photodiode having a photoactive layer which comprises a fullerene and/or a fullerene derivative, preferably PCBM, as electron-accepting compound.

Figure 1A:
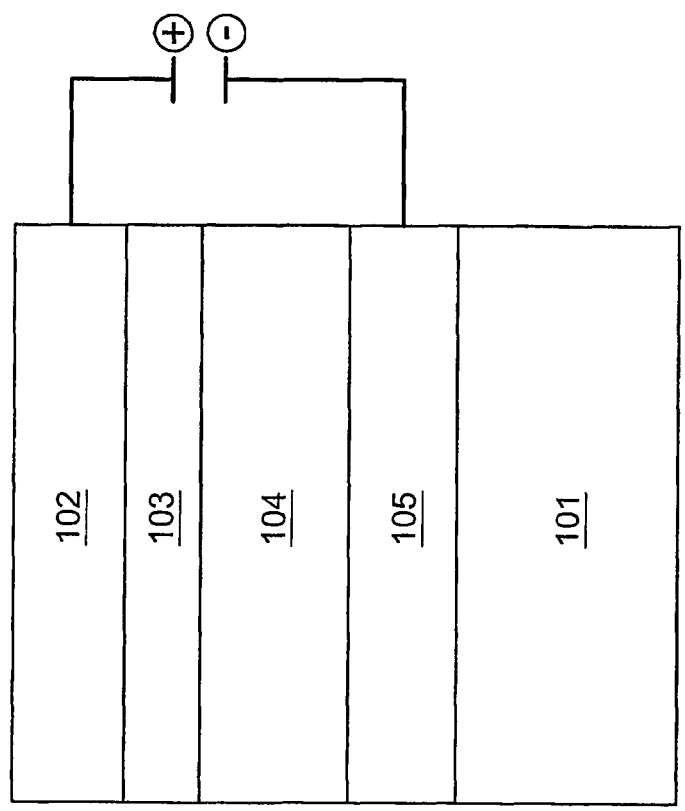

FIGS. 1A and 1B schematically show a diode. The photoactive layer in the case of an OLED is a layer with an electroluminescent compound and in the case of a photodiode is preferably a layer with an electron-donating material (p-type material) and an electron-accepting material (n-type material). The photoactive layer 104 is present between two electrodes 102 and 105. As positive and as negative electrode, materials can be used that are known per se for the use in diodes, in particular in diodes in which the active layer is based on a semi(conductive) polymer. A very suitable material as positive electrode is a high work function material, such as a metal oxide, for instance indium tin oxide (ITO), antimony tin oxide (ATO), zinc oxide, tin oxide, or a (thin) gold layer. Such materials have a good light transparency.

Very suitable as negative electrode are low work function metals, for instance calcium, ytterbium, magnesium, magnesium alloys, barium, barium alloys, lithium and lithium alloys.

These two electrodes and the photoactive layer in fact constitute the diode. Usually, these parts are present on a substrate 101. This substrate can be the carrier material for the sensor or a waveguide.

Further, between the different parts, one or more layers may be present, such as a buffer layer 103 between the positive electrode 102 and the photoactive layer 104. Very suitable as buffer layer 103 is, for instance, poly(ethylene dioxythiophene) doped with poly(sodium styrene sulfonate) (PEDOT). PEDOT as a buffer layer has been found to have a favorable effect on the efficiency, the reliability and/or the life of the diode.

Also suitable as a buffer layer is polyaniline (PANI). Optionally, over the extreme layer with respect to the substrate 101 (layer 105 in FIG. 1B, 102 in FIG. 1A) a capping layer may be provided, for instance an Al layer of at most approximately 1 µm, to protect the extreme layer.

Optionally, between the photoactive layer 104 and the negative electrode 105 an electron injection promoting layer may be present. Suitable electron injection promoting layers are, for instance, layers which comprise a phthalocyanine LiF and/or cyano-PPV.

Optionally, between the substrate and photoactive layer and/or on the outside of the substrate, a light-filtering layer may be present, which is selectively transparent to light in a particular wavelength range.

The skilled person will be able to choose suitable materials and layer thicknesses on the basis of the desired system specifications. With regard to the layer thicknesses, for instance good results have been obtained with an OLED and/or a photodiode having a positive electrode 102 of a thickness of approximately 75-300 nm, having a buffer layer 103 of approximately 50-400 nm, having a photoactive layer of approximately 50-200 nm and/or a negative electrode 105 having a thickness of approximately 50-500 nm.

Depending on the specifications, such as desired total thickness of the OLED or the photodiode and the required power, or desired detection properties, respectively, one or more of the layers can have a greater or lesser thickness than those mentioned.

The various layers are preferably selected such that the surface resistance of the positive electrode and the negative electrode is less than 20 Ohm/square.

The magnitude of the OLED surface and the photodiode surface, respectively, can be selected within a wide range, depending on the use. The surface area can be, for instance, 1 mm$^2$ or less, which is of interest in particular for use in microsensors. The lower limit is not particularly critical and can be, for instance, 1 µm or less. An OLED or photodiode can also be greater, for instance from 1 mm$^2$ to 10 cm$^2$ or more. A larger surface is for instance of interest for use in a miniaturized detection system with multiple detection channels (an array of sensors) (see for instance FIG. 3C), for instance for the simultaneous detection of different components or for the detection of more samples at the same time. As a LED in a sensor according to the invention can have a large surface, it is possible, also in a system having large numbers of detection channels and preferably also reference channels (a sensor array), to make use of one single light source for many channels, which is favorable for the stability of the measurement. A large diode surface (and hence a large measuring surface) furthermore provides an advantage with regard to the reliability of the measurement of the analysis of non-homogeneous samples.

In a preferred embodiment, the sensor comprises one or more further elements which are at least substantially made of a polymer. More preferably, at least the optical section (detection module and, if present, reference module) consists at least substantially of polymeric compound(s). Still more preferably, a sensor according to the invention consists at least substantially of plastic. For practical reasons, in particular electronics components such as a microprocessor and other components for driving the detection module and reference module and/or reading out and processing the measuring data of the photodiode(s) can be non-polymeric components. Such components are generally commercially available.

The detection module comprises preferably a sample holder. A sample holder in a sensor according to the invention consists preferably at least substantially of a polymer. Examples of sample holders are optically active layers of which an optical property (for instance photo absorption, fluorescence and/or the refractive index) changes under the influence of an interaction with a component to be detected, a cuvette and a flow-through cell.

Preferably, the sample holder in a sensor according to the invention comprises an active layer of which an optical property, such as the refractive index, the UV-VIS absorption, the fluorescence or the IR absorption, changes when the active layer is in contact with a parameter to be measured. Very good results have been obtained with a sensor where the refractive index changes under the influence of the parameter to be measured.

Suitable examples of materials for the active layer are, for instance, materials from the group consisting of ion exchangers, such as polymers with cationic and/or anionic groups such as sulfonates, carbonates, amines and other groups that are suitable for use in ion exchange chromatography (IEC), ion-selective permeable membranes and gas-selective permeable membranes.

In a preferred embodiment, a sensor according to the invention comprises an active layer of which an optical property changes as a result of the presence of a component selected from the group consisting of alcohols (in particular ethanol), carbon dioxide and ammonia, oxygen, $H^+$ and water. Suitable coatings are known per se.

A suitable coating for polar and non-polar vapors is described in "Solvatochromic betaine dyes as optochemical sensor materials: detection of polar and non-polar vapors" Dickert, F. L.; Geiger, U.; Lieberzeit, O.; Reutner, U. Sensors and Actuators B70 (2000), pp 263-269;

"Fiber-optic microsensor for high resolution pCO2 sensing in marine environment" Neurauter, G.; Klimant, I.; Wolfbeis, O. S. Fresenius J. Anal. Chem. (2000) 366, pp 481-487 describes a coating for carbon dioxide detection.

A coating for an ammonia-sensor is known from "Sol-gel based optical sensor for dissolved ammonia" Lobnik, A.; Wolfbeis, O. S. Sensors and Actuators B51 (1998), pp 203-207.

Preferably, an optical sensor according to the invention includes an organic, in particular a polymeric, reference photodiode (2, 2*b*) for measuring a reference signal coming from the above-mentioned light emitting diode of the detection module or from a second light emitting diode.

The reference diode more preferably forms part of a separate reference module. The reference module can have a design such as the detection module, with the understanding that usually no sample holder is present. The reference module optionally comprises a blank holder instead of a sample holder. The blank holder is an element resembling the sample holder, the essential difference being that no sample is present in the holder (if a cuvette or flow-through cell is involved) or is bound (if an active layer is involved). The light for the reference diode preferably comes from the same OLED as for the detection diode.

Very good results have been attained with such a sensor in which the OLED, such as a PLED, is bimodal and the reference wavelength is chosen to be on or near one $\lambda_{max}$ and the detection wavelength on or near the other $\lambda_{max}$.

Very good results have been attained with an optical sensor where the OLED, preferably a PLED, and the photodiode in the detection module and optionally the OLED and the photodiode in the reference module are connected with each other through a waveguide. The waveguide serves for guiding light from the OLED to the photodiode via the sample holder, and optionally, if applicable, via the blank holder.

On the basis of general knowledge of the art and what is described herein, the skilled person will be able to choose a suitable material and a suitable form for the waveguide.

Preferably, the waveguide consists at least substantially of plastic, more preferably the waveguide consists at least substantially of one or more transparent plastics selected from the group consisting of polycarbonates (e.g. polymethyl-methacrylate perspex), cyclic olefinic polymers (e.g. Zeonex®, Topas), polymethyl pentenes (e.g. TPX™), polymethyl-methacrylates (PMMA), polystyrenes (PS), polyamides, polyvinyl chlorides, polyethyl terephthalates, polyropylenes, styrene butadiene styrene copolymers, cellulose polymers, polyethylenes and polynorbornenes.

An advantage of plastic is the ease with which this material can be integrally processed to form a waveguide in a sensor. In addition, plastic is light in weight and usually relatively easily (de)formable without damaging the material.

As a waveguide, for instance a cylindrical transparent fiber (for instance a circular cylindrical fiber) can be used, having the OLED at one end and the photodiode at the other. A sensor with such a waveguide has been found to have a very good sensitivity.

Other examples of suitable forms are trapezoidal shapes, prisms, bar shapes and combinations thereof.

Very good results, inter alia with regard to the linear dynamic range, have been achieved with a sensor in which at least a part of the waveguide of the detection module and optionally the reference module has a trapezoidal shape with a top side (a), a base side (b) and two oblique sides (c), a sample holder (3) and blank holder (6), respectively, is in contact with the top side (a), and the light emitting diode and the photodiode are situated on opposite sides of the sample holder (3) (and blank holder, respectively) on the base side (b). An example of such a system is represented in FIG. 2.

More preferably, the top side (a) and the base side (b) are at least substantially parallel to each other. It has been found that this has a favorable effect on the efficiency with which the light generated by the OLED is guided via the sample holder/blank holder to the photodiode.

For a high efficiency with which the light generated by the OLED, such as the PLED, is guided via the sample holder/blank holder to the photodiode, it is furthermore of advantage to provide a part of the plastic waveguide with a reflecting layer, for instance with a metal such as aluminum or silver. With a trapezoidal waveguide, very good results have been obtained, for instance, when one or both oblique sides are provided with a reflecting layer.

In the case of a trapezoidal waveguide, the angle between the base side and the oblique sides can be chosen within wide limits. Preferably, this angle is less than 70°, more preferably 10° to 70°, still more preferably 20° to 50°. Very good results with regard to sensitivity and light transmission have been obtained with a sensor having a waveguide where the angle referred to is approximately 40-50°, for instance approximately 45°. Very good results regarding the linear dynamic range have been obtained with a sensor having a waveguide where the angle is approximately 10-30°, for instance 20°.

In a preferred embodiment, the detection module and—if present—the reference module, is present on or is embedded in a plastic carrier material which is provided with an electronic circuit. The electronic circuit can be formed by standard electronics, a metal, by a (semi)conductive polymer, or a combination thereof Suitable polymers as carrier material can be chosen by the skilled person on the basis of general knowledge of the art and the desired product specifications. Very suitable are inter alia liquid crystalline polymers (LCPs). LCPs are known per se. Typical examples thereof are copolymers of 4-hydroxybenzoic acid (HBA), for instance with one or more of the following compounds.

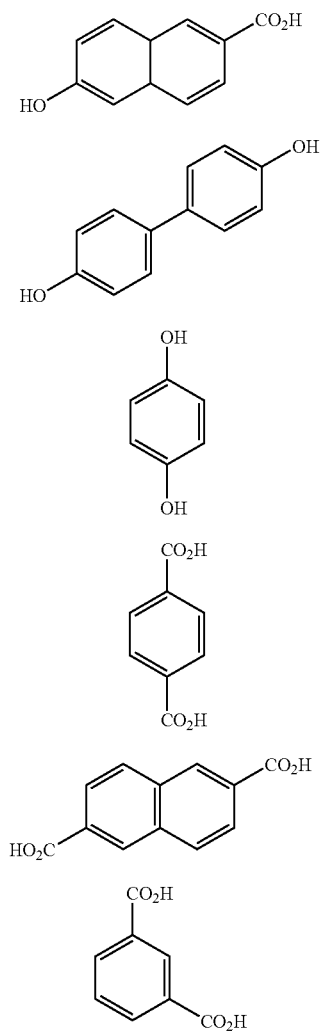

Commercially available LCPs are LCP Ticona™ and Vectra A950™.

Very suitable, furthermore, are inter alia polyamide, in particular polyamide 4,6 (such as Stanyl®) and radiation crosslinkable polyalkyl terephthalate, in particular polybutyl terephthalate (such as Vestodur® from Degussa). These polymers have a very good temperature stability, so that electronics components can be applied through (reflux) soldering.

Figure 3A:
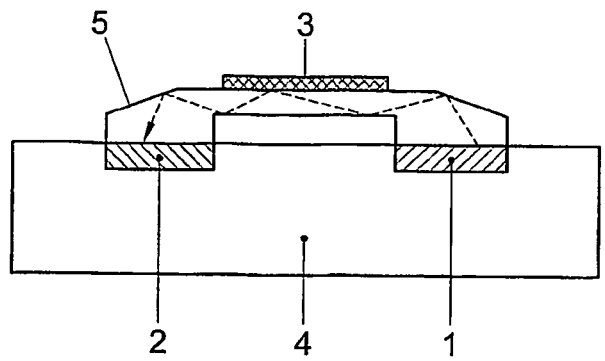
Figure 3B:
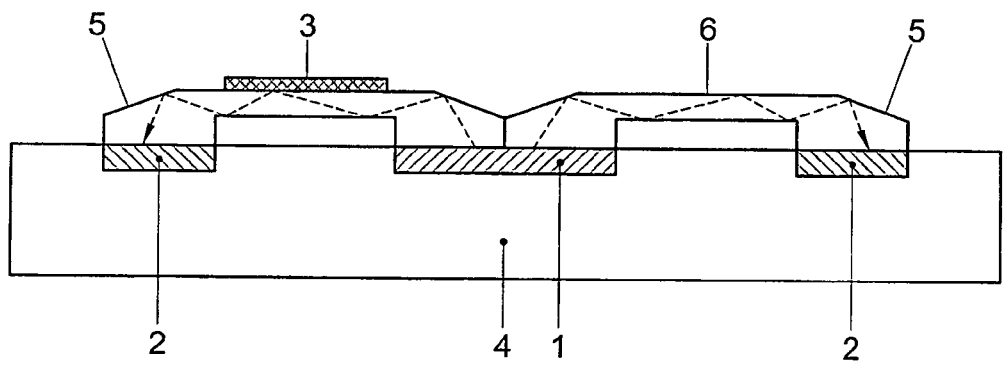

LCPs, polyamides and polyalkyl terephthalate- are furthermore very suitable because of their formability. During the manufacture, a carrier material based on one of these polymers is flexible in the sense that it can be well shaped into the desired geometry, for instance by folding as illustrated in FIGS. 3D and 3E, while it yet has a good dimensional stability when the sensor is exposed to heat.

For a good stability, it is furthermore advantageous to provide the sensor with a plastic covering layer. This layer can be of the same material as the carrier material. To reduce the influence of moisture and/or oxygen, optionally a layer of metal, metal oxide, or metal nitride can be applied to screen at least the OLED and/or the photodiode. Such a layer is preferably relatively thin with respect to the other layers. It is also possible for this purpose to use a plastic material having good oxygen and/or water barrier properties. Such materials are for instance known from WO 00/12778.

FIG. 2 schematically represents the optical section of a sensor according to the invention, with the waveguides comprising a trapezoidal portion. In FIG. 2 the detection module and the reference module are arranged parallel in line with each other. In an alternative embodiment, it is possible to arrange them parallel next to each other or at an angle. At least one OLED 1 is placed therein at one end of the waveguides 5. The OLED is preferably positioned against the waveguide.

On the waveguide 5a of the detection module, a sample holder 3 is arranged and on the waveguide 5b of the reference module, optionally a blank holder 6 is arranged. At the other end of the waveguides 5, the detection photodiode 2a and the reference photodiode 2b, respectively, are positioned. The photodiodes are preferably positioned against the waveguide. At least one or more of the oblique sides (c) of the waveguides are preferably provided with a reflective layer 7.

In a preferred embodiment, a non-transparent screen 8 is present to prevent the photodiode(s) detecting scattered light (light reaching the photodiode from the OLED via a route other than entirely via the waveguide). This screen can be a light-absorbing or reflecting material such as a non-transparent plastic. The screen can be a relatively thin layer, a block or envelop the detection module and reference module, respectively, completely with the exception of the sample holder and the reference holder, respectively.

It is furthermore an object of the invention to provide a new method with which such a sensor can be manufactured.

Accordingly, the invention also relates to a method for manufacturing an optical sensor as described herein, wherein a detection module is composed from an organic light emitting diode (1), an organic detection photodiode (2), optionally a polymeric sample holder (3) and optionally a polymeric waveguide (5). If present, a reference module is preferably composed from an organic light emitting diode (1) (which, in a preferred embodiment, is shared with the detection module), an organic reference photodiode (2), optionally a waveguide (5) and optionally an organic blank holder (6).

Preferably, at least the photodiode(s) and the OLEDs are built up integrally. Examples of processes that are suitable for integrally building up an organic photodiode or an OLED are well-known processes for manufacturing such parts. A description of a suitable process is to be found, for instance, in WO 03/026011, WO 03/022581 or WO 02/082561.

The different layers of the OLED and the photodiode can be applied with a technique known per se. The other parts can also be applied with a technique known per se. Suitable techniques in the manufacture of a sensor according to the invention are, for instance, spin coating, injection molding, extrusion, dip coating, vacuum deposition and sputtering.

Suitable printing techniques are generally known, examples being inkjet, silkscreen and offset printing. Printing is suitable in particular for applying one or more layers of the OLED and/or the photodiode, in particular the photoactive layer, the buffer layer and/or the reflector layer. Printing is also particularly suitable for applying an active layer as sample holder, the blank holder and/or the electronic circuit on the carrier material.

Suitable spin coating techniques are generally known. Spin coating is particularly suitable for applying one or more polymer-containing layers, for instance the photoactive layer and/or the buffer layer in the OLED and/or the photodiode, the active layer in the sample holder and/or the blank holder.

Suitable dip coating techniques are generally known. Dip coating is particularly suitable for the buffer layer.

Suitable injection molding techniques are generally known. Injection molding is suitable inter alia for applying a plastic covering layer, for manufacturing the waveguide(s) and for manufacturing other shaped parts. The waveguide is preferably manufactured through injection molding.

For providing the waveguide on the carrier material, injection molding is very suitable, for instance by placing the waveguide in an injection mold and circumfusing it with the polymer for the carrier material. In this way, both a screening layer can be manufactured which screens the waveguide from the ambient light, and the carrier material for the detection/reference module(s) and the electronic circuit can be formed.

Suitable vacuum deposition techniques are generally known. This technique is suitable in particular for applying metal layers and metal oxide layers, as one or more electrodes of the OLED and/or the photodiode, and one or more reflector layers (as on the waveguide), one or more barrier layers for barring water vapor, oxygen and/or other gases, in particular to protect the OLED and/or the photodiode.

Suitable sputtering techniques are generally known. Sputtering is very suitably inter alia for applying a metal oxide layer and/or a metal layer as one of the electrodes in the photodiode and/or the OLED.

For applying an electric circuit, different methods are useful. Very suitable is, for instance, a method whereby a metal layer (for instance copper, for instance in a layer thickness of approximately 5 μm) is applied from the gaseous phase onto the carrier material (for instance through chemical or physical vapor deposition (called CVD and PVD, respectively)). This metal layer can then be very suitably structured to form the desired circuit, for instance through etching or lasering. Before or after structuring, the layer can be galvanically reinforced, for instance to a thickness of ca. 30 μm with the same metal. In addition to CVD and PVD, also electroless plating is suitable to apply the metal layer.

For applying the electronic components, for instance techniques known per se such as gluing or soldering are very suitable.

Schematic representations of preferred sensors are represented in FIGS. 3A-3G. Such sensors are very suitable as a miniaturized detection system, such as a sensor on a chip. The electronic components for driving the system, recording, processing and representing the data are not represented.

The operation of the detector can be of the transmissive (see FIG. 3D) or the reflective (see FIGS. 3A, 3B, 3E, 3F and 3G) type.

Figure 3C:
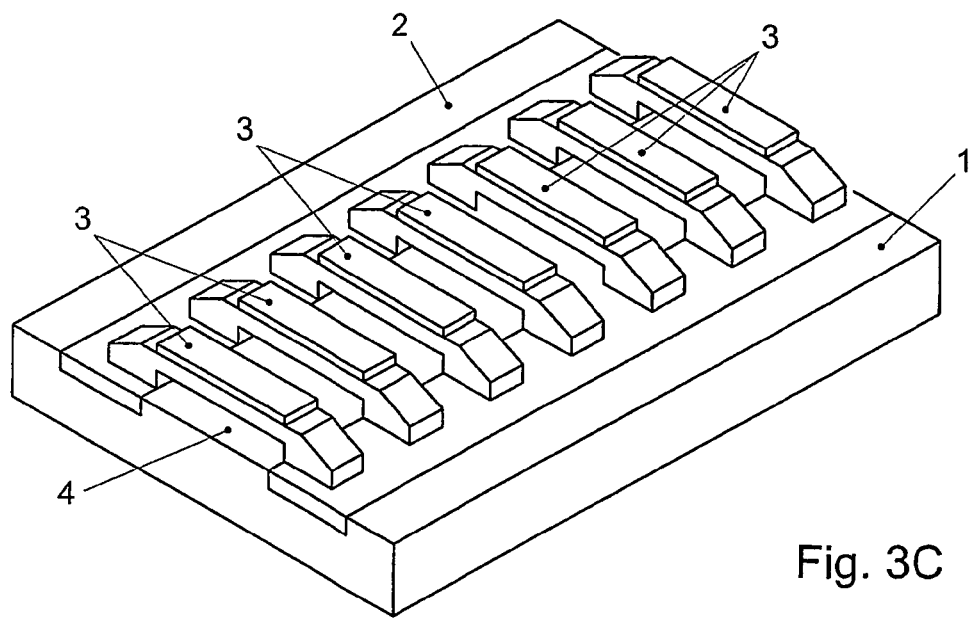
Figure 3D:
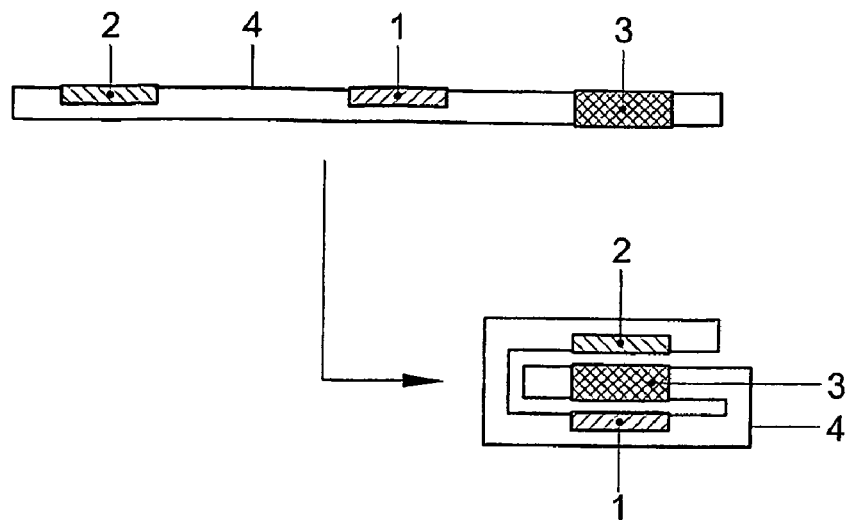
Figure 3E:
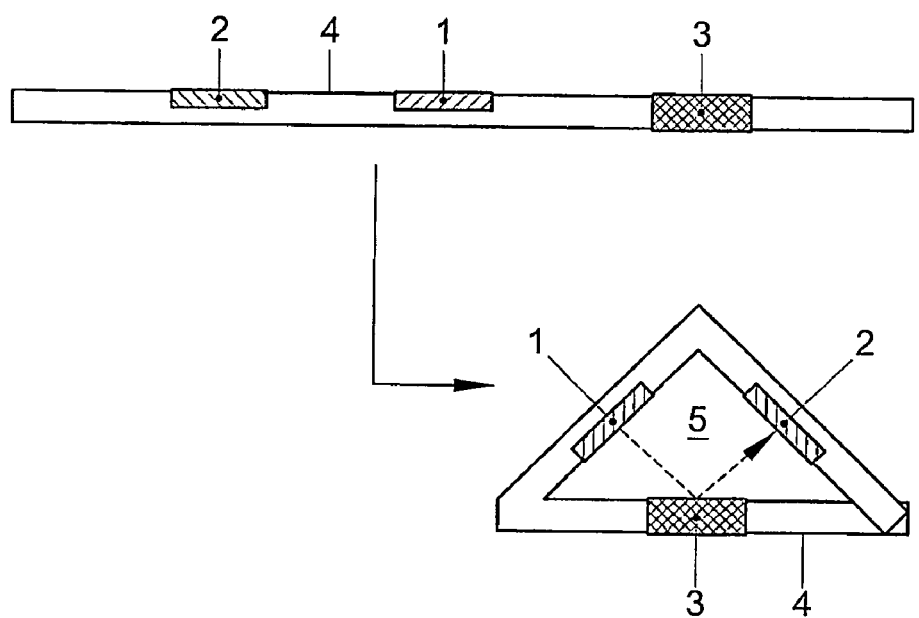

It is also possible to combine a number of detection units on one chip, a so-called array of sensors (FIG. 3C).

The numbering in the figures corresponds to the numbering in FIG. 2.

FIG. 3A shows a simple sensor with just one detection module on a carrier material. The dotted arrow indicates the light path. Under the influence of a component or physical property to be measured, an optical property in the sample holder changes, for instance the refractive index, light absorption or the fluorescence in the sample holder, which difference is measured by the photodiode.

Optionally, in the proximity of the detection photodiode, a reference diode may be present. Such a system comprises preferably, at least in the case of a photospectroscopic measurement such as light absorption or fluorescence, an OLED having at least two $\lambda_{max}$ or two OLEDs having a different $\lambda_{max}$. OLEDs having at least two $\lambda_{max}$ are described in the non-prepublished Dutch patent application NL 1023679, the content of which is hereby incorporated by reference, in particular page 9, line 5 to page 15, line 5, where suitable materials are mentioned with which an OLED can be manufactured, and page 17, line 15 to page 18, line 17, where a suitable manufacturing procedure is described which may be based on WO 03/026011, WO 03/022581 or WO 02/082561.

FIG. 3B shows a system in which further a reference module is present. The reference module enables correction for fluctuations in ambient factors such as temperature, humidity, changes in the sample composition, etc. In the embodiment shown, a single OLED is used both for the reference module and for the detection module. As a consequence, changes in the emission light intensity and/or spectral changes can also be corrected for.

FIG. 3C shows a sensor with four detection and reference modules (a so-called array). The array can have more or fewer than four detection modules and optionally more or fewer than four reference modules. In a preferred embodiment, one OLED provides the light for a number or all detection and/or reference modules. An array sensor is of interest, for instance, for simultaneous measurement of several samples or for simultaneous measurement of different components and/or physical parameters.

FIGS. 3D and 3E shows two embodiments of a type of sensor that has a particular preference, viz. a type where at least an OLED 1, a photodiode 2 and a sample holder 3 are arranged on or are arranged in a carrier material consisting of one piece. This is advantageous in particular in the manufacture, since at least the optical section of the sensor can thus be manufactured simply, for instance through folding.

FIG. 3D shows a sensor with just one module, with OLED, sample holder and photodiode arranged in one (straight) light path (see picture at bottom, right). As a result, the light from the OLED can move without directional change through the sample holder to the photodiode. The sample holder should be transparent to the detection wavelength throughout its thickness (d). The sample holder can be, for instance, a hollow channel in which a sample is provided (static) or through which a sample flows (dynamic). The walls of the channel are optionally provided with an active layer. In one embodiment, there is an opening between 1 & 3 and/or 2 & 3 as sample holder. Such a sensor can be manufactured by applying the photodiode and the OLED on or in a carrier material and providing the carrier material with a sample holder (see picture at top, left). The carrier material itself is preferably substantially not transparent, so as to prevent it from guiding light and thereby disturbing the diode. Transparency is here only desired for the sample holder 3 and the direct light path between 1, 2 and 3. By folding the carrier material as indicated in the figure, the sensor is formed. In addition to providing an advantage in the manufacture, an embodiment as shown in FIG. 3D further affords the possibility of providing an extremely thin sensor.

FIG. 3E shows a sensor of a prism shape (see right-hand picture). For a better dimensional stability, the central space is preferably provided with a transparent prism which then serves as waveguide 5. This sensor can be formed from a flexible carrier material which is provided with OLED, photodiode and sample holder.

Optionally, in the proximity of the detection photodiode, a reference diode can be present. Such a system preferably comprises an OLED with at least two $\lambda_{max}$ or two OLEDs having a different $\lambda_{max}$.

Figure 3F:
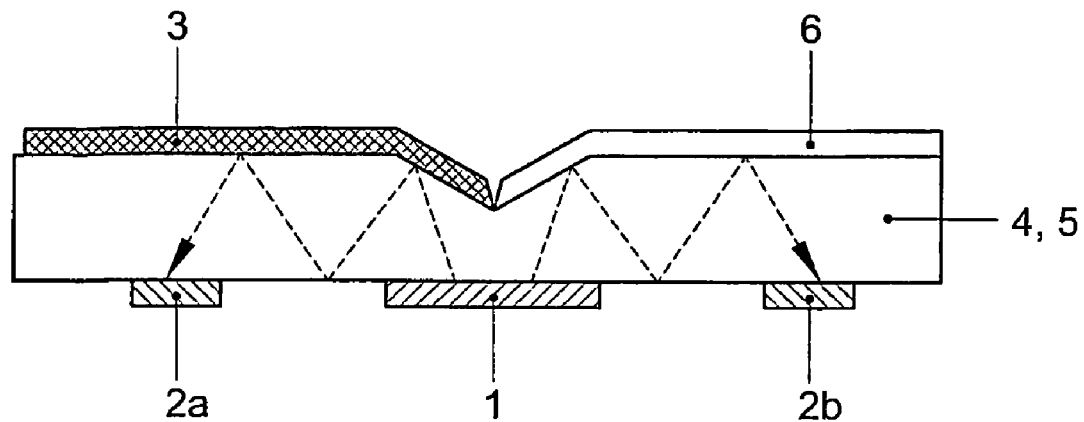

In FIG. 3F the carrier material is at the same time waveguide.

Figure 3G:
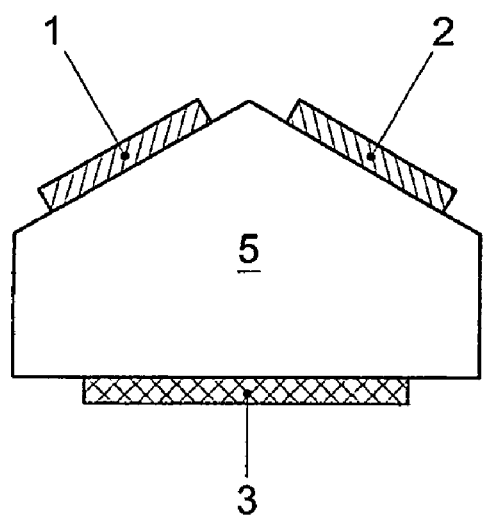

FIG. 3G shows the optical section of a sensor having one photodiode 2 and two OLEDs 1. The waveguide 5 here further carries the OLEDs 1, the photodiode 2 and the sample holder 3. The waveguide is formed by a rectangular portion and a trapezoidal portion. The OLEDs are arranged on the oblique sides (c) of the trapezoidal portion and the photodiode is placed therebetween, at the top side (a). One OLED serves for generating the detection light and the second OLED for generating the reference light. The wavelength of the detection light differs from that of the reference signal. The wavelength of the detection light is chosen such that this light is absorbed in the sample holder to an extent that depends on the amount or concentration of the component to be measured or the magnitude of the physical parameter, while the reference wavelength is chosen such that the absorption of this light is essentially independent of the amount or concentration of the component to be measured or the magnitude of the physical parameter and is preferably as low as possible. By presently allowing the detection OLED and the reference OLED to shine alternately, the photodiode can measure both a detection signal and a reference signal.

The invention further relates to the use of an optical sensor for detecting a component or a physical parameter in a liquid, preferably an aqueous medium or a gas, preferably air. In particular, the invention relates to the use of a disposable sensor for detecting a component or physical parameter, the sensor serving for single-time use.

Preferred uses comprise the detection of a component selected from the group consisting of alcohols, in particular ethanol, carbon dioxide, ammonia, oxygen, $H^+$ (pH) and water.

The invention will presently be illustrated in and by a few examples.

EXAMPLE 1

Sensor for Determination of Ethanol

On a waveguide for a sensor as represented in any one of the figures, an ethanol-sensitive coating was applied as follows.

A solution A was prepared by dissolving 15 g of dry polyvinyl chloride (PVC) in 95 ml of tetrahydrofuran (THF) (PVC content of 15% w/v).

A solution B was prepared by dissolving 1.2 g of Crystal Violet Lacton and 2.6 g of bisphenol A in 50 ml of THF.

A solution C was prepared by mixing 10 ml of solution A with 2 ml of solution B and 2 ml of 2-nitrophenyloctylether.

Solution C was applied to a transparent carrier (Zeonex® waveguide) by spin coating or by pouring.

The waveguide with coating was assembled with a polymeric LED having a good light emission at 610 nm and a polymeric photodiode having a good light sensitivity at 610 nm. The measured absorption at 610 nm is inversely proportional to the ethanol concentration.

Manufacture of a LED

A glass carrier material was provided with a transparent layer of indium tin oxide (ITO) (commercially available e.g. from Baltzers) by sputtering to a layer thickness of ca. 150 nm and a surface resistance of maximally 20 Ω/square. On the ITO a ca. 200 nm thick layer of PEDOT (Baytron P from Bayer) was applied by spin coating (1,000-3,000 rpm, 1 min. of drying at 180° C.).

Next, by means of spin coating of a 0.5% (w/v) solution of

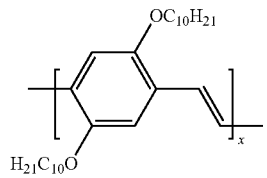

in toluene, the electroluminescent layer of ca. 100 nm was manufactured. On the active layer, first a Barium electrode layer of 10 nm, followed by an aluminum covering layer of a thickness of ca 150 nm was applied by means of vacuum deposition. The surface of the LED was ca. $0.9\ cm^2$.

Manufacture of a Photodiode

Similarly to LED, but with a mixture of 80% of PCBM with 20% of the above-mentioned polymer as active layer. As electrode, a layer of 2-5 nm LiF with a covering layer of aluminum is used.

EXAMPLE 2

Sensor for Determination of $CO_2$

A solution A was prepared by dissolving 200 mg of 8-hydroxypyrene-1,3,6-trisulfonic acid (HPTS) in 10 mM NaOH.

A solution B was prepared by dissolving 850 mg of tetraoctyl ammonium bromide (TOA-bromide) in 35 ml of methylene chloride.

Solution A was added to solution B and together they were stirred for at least 1 hour.

Then, the stirred liquid was shaken for separating the organic phase from the aqueous phase. The organic phase having therein the HPTS-TOA ion pair was washed twice with 50 ml of 10 mM NaOH, after which the organic phase was evaporated to obtain HPTS-TOA.

3 g of ethyl cellulose were dissolved in an ethanol/toluene mixture (20/80 v/v). To the solution were added 6 mg of HPTS-TOA.

The resultant solution was applied to the transparent carrier (as described in Example 1).

The $CO_2$ concentration can be determined with the aid of this coating by fluorescence, with an excitation wavelength of about 470 nm, while determining the emission in an emission window between 510 nm and 570 nm.

EXAMPLE 3

Sensor for Determination of the pH

A solution A was prepared by dissolving 620 mg of cellulose acetate in 15 ml of acetone.

A solution B was prepared by dissolving 5 mg of tris(4,7-biphenyl-1,10-phenanthroline) Ruthenium (II) Chloride, 50 mg of thymol blue and 50 mg of tetradodecyl ammonium tetrakis (4-chlorophenyl) borate in 15 manual of acetone.

A solution C was prepared by adding 5 ml of solution A to 1 ml of solution B and adding 4 ml of acetone.

A solution D was prepared by mixing 1 ml of nafion solution (Aldrich 66796-30-3) with 4 ml of isopropyl alcohol.

Solution C was poured onto the transparent carrier (as described in Example 1) and dried. Then an overcoating was applied by applying solution D by pouting or spin coating. The pH can be determined on the basis of a fluorescent life-time at an excitation of 470 nm in an emission window between 510 and 570 nm. The fluorescence life-time increases with increasing pH in the range of pH 4.5-8.

The invention claimed is:

1. An optical sensor, comprising:
   a fully disposable detection module, which detection module comprises an organic light emitting diode and an organic detection photodiode for measuring emitted light which during the use of the sensor reaches the photodiode via a sample holder, the sample holder containing an active layer of which an optical property changes when the active layer is in contact with a component to be measured, and the sensor being of the reflective type, wherein the organic light emitting diode, the organic detection photodiode and the sample holder are all situated on or in a single flexible carrier material; and
   an organic reference photodiode for measuring a reference signal coming from said light emitting diode of the detection module or from a second light emitting diode, wherein the reference photodiode forms part of a reference module, which reference module further comprises a blank holder.

2. The optical sensor according to claim 1, wherein the photodiode is a photovoltaic cell.

3. The optical sensor according to claim 1, wherein the light emitting diode and the photodiode in the detection module and the reference photodiode in the reference module are connected with each other through a plastic waveguide.

4. The optical sensor according to claim 3, wherein at least a part of the waveguide has a trapezoidal shape with a top side (a), a base side (b) and two oblique sides (c), the sample holder is situated at the top side (a), and the light emitting diode and the photodiode are situated on opposite sides of the sample holder on the base side (b).

5. The optical sensor according to claim 4, wherein the top side (a) and the base side (b) are at least substantially parallel to each other.

6. The optical sensor according to claim 4, wherein at least one of the oblique sides of the plastic waveguide is provided with a reflecting layer.

7. The optical sensor according to claim 4, wherein the angle between the base side and at least one oblique side is 10-70°.

8. The optical sensor according to claim 4, wherein the waveguide comprises at least substantially one or more plastics selected from a group consisting of polycarbonates (e.g. polymethylmethacrylate perspex), cyclic olefinic polymers (e.g. Zeonex®, Topas), polymethyl pentenes (e.g. TPX™), polymethyl-methacrylates (PMMA), polystyrenes (PS), polyamides, polyvinyl chlorides, polyethyl-terephthalates, polypropylenes, styrene butadiene styrene copolymers, cellulose polymers, polyethylenes and polynorbornenes.

9. The optical sensor according to claim 1, wherein the light emitting diode is a polymeric light emitting diode, having in the photoactive layer as electroluminescent compound a polymer selected from a group consisting of polyarylene compounds, poly(paraphenylene vinylene) compounds, polyfluorene compounds, polyacetylene compounds, polythiophene compounds, polypyrroles, polyanilines, including derivatives of said polymers, copolymers of said polymers and said polymers provided with a dye.

10. The optical sensor according to claim 1, wherein one of the detection photodiode and the reference photodiode is a polymeric photodiode, having in the photoactive layer a polymer selected from the group consisting of polyarylene compounds, poly(paraphenylene vinylene) compounds, polyfluorene compounds, polyacetylene compounds, polythiophene compounds, polypyrroles, polyanilines, including derivatives of said polymers, copolymers of said polymers and said polymers provided with a dye.

11. The optical sensor according to claim 1, wherein the sample holder contains an active layer of which at least one of the refractive index, the UV-VIS absorption, the fluorescence or the IR absorption, changes when the active layer is in contact with a component to be measured.

12. The optical sensor according to claim 11, wherein the active layer is selected from the group consisting of ion exchangers, ion-selective permeable membranes and gas-selective permeable membranes.

13. The optical sensor according to claim 11, wherein the optical property of the active layer changes as a result of the presence of a component selected from the group consisting of alcohols, in particular ethanol, carbon dioxide, ammonia, oxygen and water.

14. The optical sensor according to claim 1, comprised substantially of plastic.

15. An array of optical sensors each sensor comprising a fully disposable detection module, which detection module comprises an organic light emitting diode and an organic detection photodiode for measuring emitted light which during the use of the sensor reaches the photodiode via a sample holder, the sample holder containing an active layer of which an optical property changes when the active layer is in contact with a component to be measured, and the sensor being of the reflective type, wherein the organic light emitting diode, the organic detection photodiode and the sample holder are all situated on or in a single flexible carrier material; and
   an organic reference photodiode for measuring a reference signal coming from said light emitting diode of the detection module or from a second light emitting diode, wherein the reference photodiode forms part of a reference module, which reference module further comprises a blank holder.

16. A method for manufacturing an optical sensor comprising:
   providing a fully disposable detection module comprised of a single flexible carrier, a sample holder containing an active layer of which an optical property changes when the active layer is in contact with a component to be measured, the detection module being of the reflective type, the detection module further comprising an organic light emitting diode;
   associating the detection module with an organic detection photodiode, wherein the organic light emitting diode, the organic detection photodiode and the sample holder are all situated on or in the single flexible carrier; and
   providing an organic reference photodiode for measuring a reference signal coming from said light emitting diode of the detection module or from a second light emitting diode, wherein the reference photodiode forms part of a reference module, which reference module further comprises a blank holder.

17. The, method according to claim 16, wherein one of the light emitting diode and the photodiode is manufactured by means of injection molding, printing, dip coating, vacuum deposition or spin coating.

18. The method according to claim 16, wherein the diodes are manufactured on at least one of a surface of a waveguide, a surface of the single flexible carrier material for the detection module, an electronic circuit and the reference module.

19. The method according to claim 16, wherein the detection module is built up integrally.

20. The method according to claim 16, wherein the light emitting diode and the detection photodiode are provided in association with the single flexible carrier material and the single flexible carrier material is then folded.

21. The method according to claim 16, wherein the sensor is provided with one of a plastic and metal covering layer, and the sample holder remains at least substantially free of the covering layer.

* * * * *